(12) United States Patent
Yamada et al.

(10) Patent No.: US 11,758,860 B2
(45) Date of Patent: Sep. 19, 2023

(54) ALGA GROWING APPARATUS AND ALGA GROWING METHOD

(71) Applicants: NICHIMAN CO., LTD., Ibusuki (JP); DAISHIN CO., LTD., Ibusuki (JP)

(72) Inventors: Kenichi Yamada, Ibusuki (JP); Satoshi Nakamura, Ibusuki (JP); Tsuyoshi Nakamura, Ibusuki (JP); Kazumitsu Toya, Nagoya (JP)

(73) Assignees: NICHIMAN CO., LTD., Ibusuki (JP); DAISHIN CO., LTD., Ibusuki (JP)

( * ) Notice: Subject to any disclaimer, the term of this patent is extended or adjusted under 35 U.S.C. 154(b) by 0 days.

(21) Appl. No.: 17/059,155

(22) PCT Filed: Sep. 13, 2019

(86) PCT No.: PCT/JP2019/036047
§ 371 (c)(1),
(2) Date: Nov. 25, 2020

(87) PCT Pub. No.: WO2020/213189
PCT Pub. Date: Oct. 22, 2020

(65) Prior Publication Data
US 2022/0022393 A1    Jan. 27, 2022

(30) Foreign Application Priority Data
Apr. 19, 2019  (JP) ................................ 2019-080450

(51) Int. Cl.
*A01G 33/00*    (2006.01)
*A01G 7/04*     (2006.01)

(52) U.S. Cl.
CPC ............. *A01G 33/00* (2013.01); *A01G 7/045* (2013.01)

(58) Field of Classification Search
CPC ...................................................... A01G 33/00
See application file for complete search history.

(56) References Cited

U.S. PATENT DOCUMENTS

| | | | |
|---|---|---|---|
| RE24,822 E * | 5/1960 | Pallotta et al. | C12M 27/10 435/298.2 |
| 4,600,694 A * | 7/1986 | Clyde | C12M 39/00 435/298.2 |

(Continued)

FOREIGN PATENT DOCUMENTS

| CN | 102021119 A | 4/2011 |
|---|---|---|
| JP | 2007-512025 A | 5/2007 |

(Continued)

*Primary Examiner* — Joshua D Huson
*Assistant Examiner* — Megan J Moroney
(74) *Attorney, Agent, or Firm* — Heedong Chae; Lucem, PC (57) ABSTRACT

An alga growing apparatus that includes a gas dissolving portion, an alga tank, first and second LEDs, a supplying portion, and a circulation pump portion. Gas dissolving portion dissolves carbon dioxide and oxygen into deep-ocean water to form growing water. The circulation pump portion sucks out and delivers the growing water and the nori thalli from the alga tank 30 to the gas dissolving portion and injects the growing water and the nori thalli into the alga tank upon passage through the gas dissolving portion and a supply pipe of the supplying portion. The supplying portion discharges the growing water and the nori thalli along a direction obliquely intersecting a curving direction of an inner side surface of the alga tank and the growing water flows inside the alga tank as an eddy flow.

6 Claims, 4 Drawing Sheets

(56) References Cited

U.S. PATENT DOCUMENTS

| | | | | |
|---|---|---|---|---|
| 4,872,985 | A * | 10/1989 | Dinges | A01G 31/00 210/602 |
| 6,156,561 | A * | 12/2000 | Kodo | C12M 23/58 435/946 |
| 6,391,238 | B1 * | 5/2002 | Sato | C05D 9/00 264/141 |
| 8,642,326 | B1 * | 2/2014 | Schaefer | C12M 21/02 435/257.1 |
| 8,685,707 | B2 * | 4/2014 | Ploechinger | B32B 5/12 435/243 |
| 10,368,507 | B2 * | 8/2019 | Van Wingerden | A01G 31/02 |
| 10,624,275 | B1 * | 4/2020 | Lewis | A01G 9/247 |
| 10,907,127 | B2 * | 2/2021 | Hazlebeck | C12M 23/18 |
| 10,934,567 | B2 * | 3/2021 | Tachibana | C12N 1/02 |
| 11,129,339 | B2 * | 9/2021 | Spiro | A01G 9/0293 |
| 11,310,976 | B1 * | 4/2022 | Cross | A01G 31/047 |
| 2005/0120624 | A1 | 6/2005 | Levy | |
| 2008/0083160 | A1 * | 4/2008 | Levy | A01G 33/00 47/1.4 |
| 2010/0236135 | A1 * | 9/2010 | Kleinberger | C12M 21/02 435/292.1 |
| 2011/0308149 | A1 * | 12/2011 | Hazlebeck | C12M 21/02 47/1.4 |
| 2014/0322805 | A1 * | 10/2014 | Hazlebeck | C12M 27/02 435/292.1 |
| 2015/0173317 | A1 * | 6/2015 | Ordway | A01G 33/00 435/286.5 |
| 2015/0267162 | A1 * | 9/2015 | Kanehara | A01G 33/00 435/257.1 |
| 2016/0029579 | A1 * | 2/2016 | Carscallen | A01G 9/249 47/62 R |
| 2017/0318764 | A1 * | 11/2017 | Hazlebeck | C12N 1/12 |

FOREIGN PATENT DOCUMENTS

| | | |
|---|---|---|
| JP | 2011-229402 A | 11/2011 |
| JP | 2011-230066 A | 11/2011 |
| JP | 2012-213351 A | 11/2012 |
| JP | 2012213351 A * | 11/2012 |
| JP | 2014-036596 A | 2/2014 |
| JP | 2016-208925 A | 12/2016 |
| JP | 2016208925 A * | 12/2016 |
| TW | 201811169 | 4/2018 |

* cited by examiner

ALGA GROWING APPARATUS AND ALGA GROWING METHOD

BACKGROUND

Field of the Invention

The present invention relates to an alga growing apparatus and an alga growing method. Specifically, the present invention relates to an alga growing apparatus and an alga growing method for growing, for example, nori.

Background Art

Whereas culture of seaweed, for example, nori is carried out at sea, nori seaweed production by sea culture is decreasing due to increase in seawater temperature, etc.

In Japan, there are present numerous foods in which nori is used, such as norimaki, sushi, onigiri, etc., and because nori is indispensable for Japanese food, the decrease in nori seaweed production is a serious problem.

Thus in order to resolve such problems of sea culture, culturing of algae on land where receiving of influences of the natural environment is unlikely is being proposed.

Figure 4:
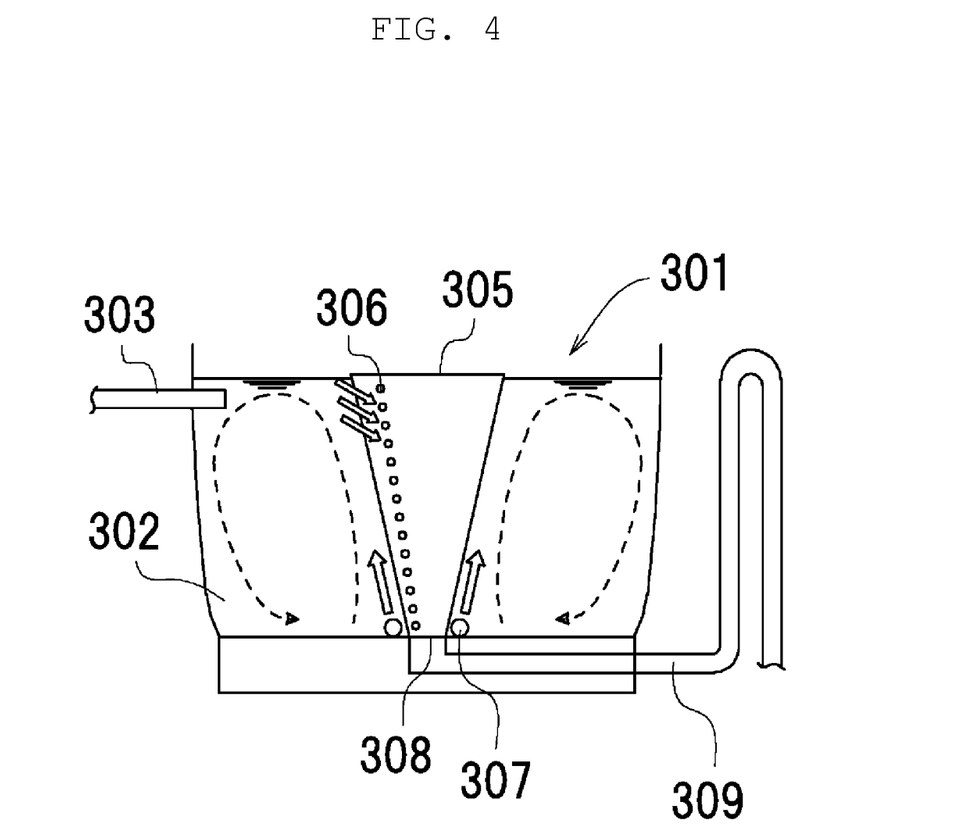
FIG. 4 is a schematic view showing a conventional seaweed culture apparatus.

For example, a seaweed culture apparatus shown in FIG. 4 is described in Patent Literature 1.

That is, the seaweed culture apparatus 301 described in Patent Literature 1 includes, as a main body thereof, a water tank 302 of circular cylindrical shape with bottom having an opening portion formed at an upper portion.

Also, a water filling pipe 303 is mounted in communication with a vicinity of the upper opening portion of the water tank 302.

Also, a cylindrical body 305 that is a cylindrical member of substantially truncated conical shape is disposed in an interior of the water tank 302.

Also, a plurality of open holes 306 are formed across an entirety of the cylindrical body 305 in an up/down direction.

Also, an air stone 307 connected to an unillustrated external air pump is disposed in a vicinity of an outer periphery of the cylindrical body 305 at a lower portion of the water tank 302. Here, the air stone 307 is an aeration mechanism.

Also, a water inlet 308 is formed at a lower portion of the water tank 302 at an inner side of the cylindrical body 305.

Also, a piping 309 is in communication with the water inlet 308. When a water level of seawater inside the water tank 302 reaches a desired water level, draining through the piping 309 is performed and the water level in the water tank is kept fixed.

CITATION LIST

Patent Literature

Patent Literature 1: Japanese Published Unexamined Patent Application No. 2014-036596

SUMMARY OF THE INVENTION

Technical Problem

However, with the apparatus described in Patent Literature 1, an aeration system is adopted and carbon dioxide or oxygen is not dissolved sufficiently into the seawater. This is because although air bubbles are formed with the aeration system, the air bubbles are formed because gases are not dissolved sufficiently into the seawater.

Also, air bubbles do not stay at a bottom layer portion and therefore, carbon dioxide or oxygen is not supplied sufficiently to algae at the bottom layer portion of the water tank.

Consequently, growing efficiency of algae is not sufficient.

The present invention has been made in view of the above points and an object thereof is to provide an alga growing apparatus and an alga growing method that are capable of improving growing efficiency of algae.

Solution to Problem

To achieve the above object, an alga growing apparatus according to the present invention includes a gas dissolving portion capable of dissolving carbon dioxide into a liquid to form a solution, an alga tank capable of containing the solution and algae placed in the solution and with which an inner side surface in contact with the solution and the algae that are contained is curved, a light emitter capable of emitting light toward an interior of the alga tank in which the solution and the algae are contained, a supplying portion being in communication with the gas dissolving portion and the alga tank and capable of discharging the solution along a curving direction of the inner side surface of the alga tank or along a direction obliquely intersecting the curving direction, and a circulation pump portion being in communication with the alga tank and the gas dissolving portion, capable of sucking out the solution and the algae contained in the alga tank from the alga tank, and capable of injecting the sucked-out solution and algae from the supplying portion into the alga tank through the gas dissolving portion.

Here, photosynthesis can be promoted inside the alga tank by the gas dissolving portion capable of dissolving the carbon dioxide into the liquid to form the solution, the light emitter capable of emitting light toward the interior of the alga tank containing the solution and the algae, and the circulation pump portion being in communication with the alga tank and the gas dissolving portion, capable of sucking out the solution and the algae contained in the alga tank from the alga tank, and capable of injecting the sucked-out solution and algae from the supplying portion into the alga tank through the gas dissolving portion.

The "liquid" handled by the gas dissolving portion shall include a liquid into which the carbon dioxide is yet to be dissolved by the gas dissolving portion and a liquid into which the carbon dioxide has already been dissolved by the gas dissolving portion.

Also, an eddy flow of the solution can be generated inside the alga tank and the light from the light emitter can be illuminated uniformly onto the algae by the alga tank capable of containing the solution and the algae placed in the solution and with which the inner side surface in contact with the solution and the algae that are contained is curved and the supplying portion being in communication with the gas dissolving portion and the alga tank and capable of discharging the solution along the curving direction of the inner side surface of the alga tank or along the direction obliquely intersecting the curving direction.

Also, by the eddy flow, oxygen bubbles formed by photosynthesis are easily separated from the algae and the algae are thereby enabled to absorb the carbon dioxide easily.

Also, the algae and the solution are passed through the gas dissolving portion together by the circulation pump portion that is in communication with the alga tank and the gas dissolving portion, is capable of sucking out the solution and the algae contained in the alga tank from the alga tank, and is capable of injecting the sucked-out solution and algae from the supplying portion into the alga tank through the gas dissolving portion and therefore, the carbon dioxide can be supplied sufficiently to the algae in the gas dissolving portion.

Also, the alga growing apparatus according to the present invention may be arranged such that the alga tank has a circular cylindrical shape extending in one direction with both ends in the direction of extension being closed and the supplying portion has a supply pipe that is connected in communication with a penetrating hole formed in the inner side surface of the alga tank and putting the interior and an exterior of the alga tank in communication and a cover body that is disposed on a penetrating hole central axis extending in a direction substantially orthogonal to a line joining opposing edge portions of the penetrating hole, is mounted to the inner side surface of the alga tank, forms, with the inner side surface, a space in communication with the supply pipe, has formed therein an opening portion putting the space and the interior of the alga tank in communication and facing a direction intersecting the direction of extension of the alga tank, and with which a surface at an opposite side to a surface facing the space is curved.

In this case, the algae are less likely to become caught in the supplying portion than an arrangement not having the cover body and with which the supply pipe is projected from the inner side surface of the alga tank.

Also, the alga growing apparatus according to the present invention with which the alga tank extends in one direction may be arranged such that a plurality of the light emitters are arrayed in series at predetermined intervals from each other in the same direction as the direction of extension of the alga tank, there are a plurality of serial arrays of the light emitters, and the number of light emitters on a line substantially orthogonal to the direction of extension of the alga tank and connecting two arrays that oppose each other is one.

In this case, a light emitting capability can be maintained while suppressing a size per unit of the light emitters and the number of the light emitters.

Also, the alga growing apparatus according to the present invention with which the alga tank extends in one direction may be arranged such that the alga tank is disposed in a state where the direction of extension of the alga tank intersects a horizontal direction, a sucking-out part that is a part at which the solution and the algae are sucked out is formed at one end portion of the alga tank, a position of the one end portion of the alga tank at which the sucking-out part is formed is located lower in a vertical direction than a position of another end portion at an opposite side to the one end portion, and the direction that the opening portion of the cover body faces is a direction obliquely intersecting the direction of extension of the alga tank and is a direction directed toward the one end portion of the alga tank.

In this case, the position of the one end portion of the alga tank at which the sucking-out part is formed is located lower in the vertical direction than the position of the other end portion at the opposite side to the one end portion, that is, the alga tank is inclined and since the solution flows out from the opening portion of the cover body toward the one end portion of the alga tank, the algae gather easily toward the sucking-out part due to gravity and a force of flow of the solution, and the solution and the algae can be circulated even if a length of extension of the alga tank is made comparatively long.

The "end portions of the alga tank" as referred to in the present invention shall include not just the closed portions, that is, surface portions substantially orthogonal to the direction of extension of the alga tank but also regions spreading from the closed portions to predetermined ranges in the direction of extension of the alga tank.

Also, the alga growing apparatus according to the present invention may be arranged such that the gas dissolving portion is capable of forming a solution having a high pressure than a pressure of the exterior of the alga tank.

In this case, an air layer is unlikely to form inside the alga tank. Also, unwanted bacteria, etc., are unlikely to flow into the alga tank from the exterior of the alga tank.

Also, the alga growing apparatus according to the present invention may be arranged to include a liquid fertilizer injecting portion in communication with the supplying portion and capable of injecting a liquid fertilizer into the supplying portion, a liquid injecting portion in communication with the gas dissolving portion and capable of injecting a liquid into the gas dissolving portion, and a control valve that is mounted to a communicating pipe connecting the gas dissolving portion, the alga tank, the supplying portion, the circulation pump portion, the liquid fertilizer injecting portion, and the liquid injecting portion in mutual communication and to an opening portion putting the interior and the exterior of the alga tank in communication or an unloading pipe connected in communication with the opening portion and is capable of being controlled based on a signal transmitted by a portable terminal.

In this case, a flow rate of the solution passing through the communicating pipe can be controlled or an unloading amount of the solution from the alga tank can be controlled by a single operation of the portable terminal.

Also, when a plurality of alga tanks are present, a workload can be lightened.

Also, in order to achieve the above object, an alga growing method according to the present invention includes a solution forming step of forming a solution by dissolving carbon dioxide having a higher pressure than a pressure of a liquid into the liquid in a gas dissolving portion capable of dissolving the carbon dioxide into the liquid, a discharging step of supplying the solution to an alga tank having a curved inner side surface and making the solution flow along the inner side surface of the alga tank, a nori thalli supplying step of supplying nori thalli to the alga tank, a light emitting step of emitting light toward an interior of the alga tank containing the solution and the nori thalli placed in the solution, and a circulating step of sucking out the solution and the nori thalli from the alga tank and introducing the solution and the nori thalli into the gas dissolving portion.

Here, photosynthesis can be promoted inside the alga tank by the solution forming step of forming the solution by dissolving the carbon dioxide having the higher pressure than the pressure of the liquid into the liquid in the gas dissolving portion capable of dissolving the carbon dioxide into the liquid, the light emitting step of emitting light toward the interior of the alga tank containing the solution and the nori thalli placed in the solution, and the circulating step of sucking out the solution and the nori thalli from the alga tank and introducing the solution and the nori thalli into the gas dissolving portion.

Also, an eddy flow of the solution can be generated inside the alga tank and the light from a light emitter can be illuminated uniformly onto the nori thalli by the discharging step of supplying the solution to the alga tank having the curved inner side surface and making the solution flow along the inner side surface of the alga tank.

Also, by the eddy flow, oxygen bubbles formed by photosynthesis are easily separated from the nori thalli and the nori thalli are thereby enabled to absorb the carbon dioxide easily.

Also, it shall be deemed that there are cases where when the solution is made to flow, the nori thalli also flow together. Also, by the nori thalli supplying step of supplying the nori thalli to the alga tank, the nori thalli are used and therefore, growing can be completed faster than a method of cultivating by supplying spores or protonemata of nori.

Also, by the circulating step of sucking out the solution and the nori thalli from the alga tank and introducing the solution and the nori thalli into the gas dissolving portion, the nori thalli are introduced together with the solution into the gas dissolving portion and therefore, the carbon dioxide can be supplied sufficiently to the nori thalli in the gas dissolving portion.

Also, the alga growing method according to the present invention may be arranged such as to include an unloading step of unloading the nori thalli from the alga tank and a cutting step of cutting the unloaded nori thalli and arranged such that in the nori thalli supplying step, nori thalli having a length shorter than a length of the nori thalli unloaded in the unloading step are supplied.

In this case, a portion of the grown nori thalli can be reused and the nori thalli can be cultivated semi-permanently.

Advantages of the Invention

The alga growing apparatus according to the present invention can improve growing efficiency of algae.

The alga growing method according to the present invention can improve the growing efficiency of algae.

DESCRIPTION OF THE EMBODIMENTS

Embodiments of the present invention shall now be described with reference to the drawings to contribute to an understanding of the present invention.

Figure 1:
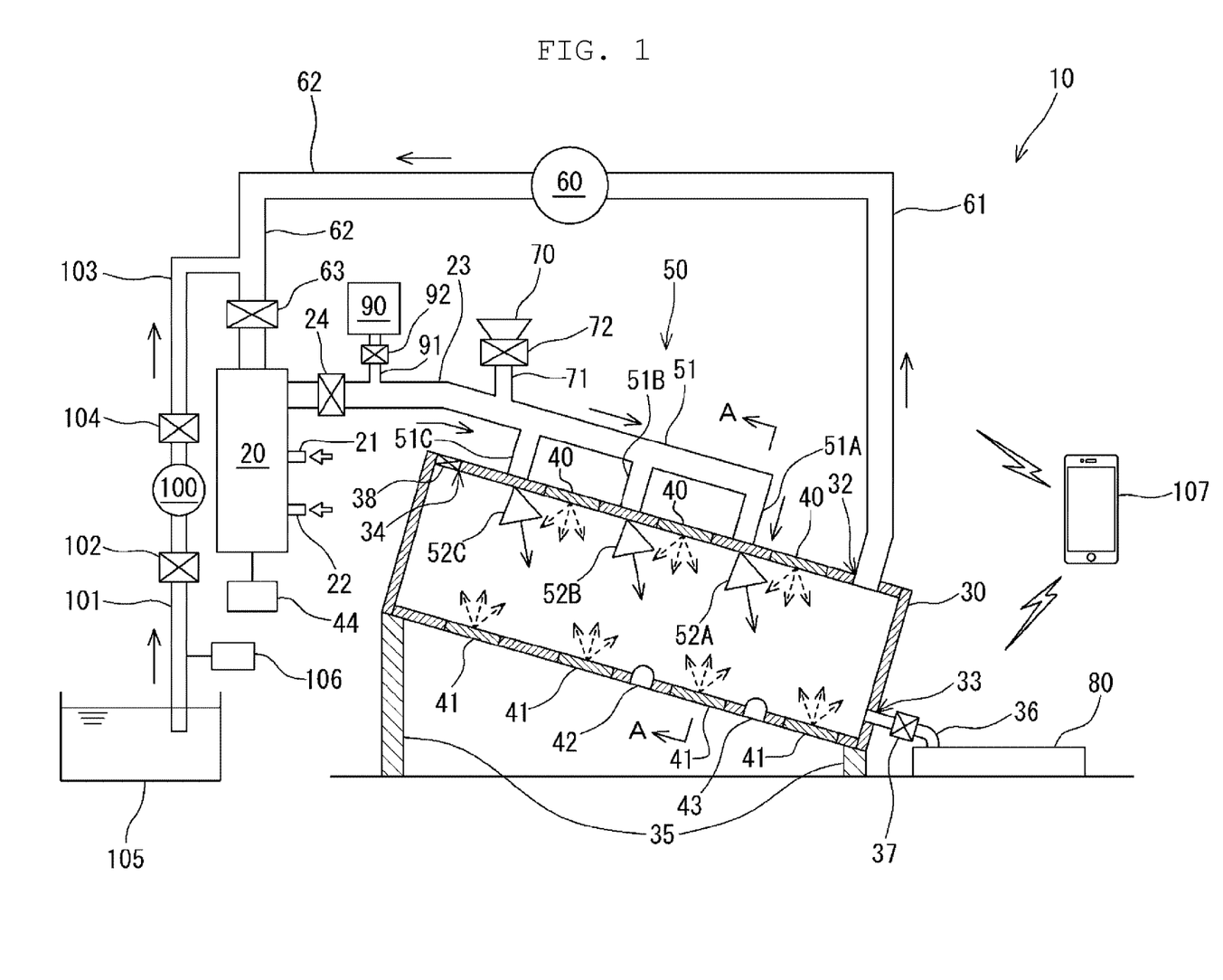
FIG. 1 is a schematic view for describing an example of an alga growing apparatus to which the present invention is applied.
Figure 2:
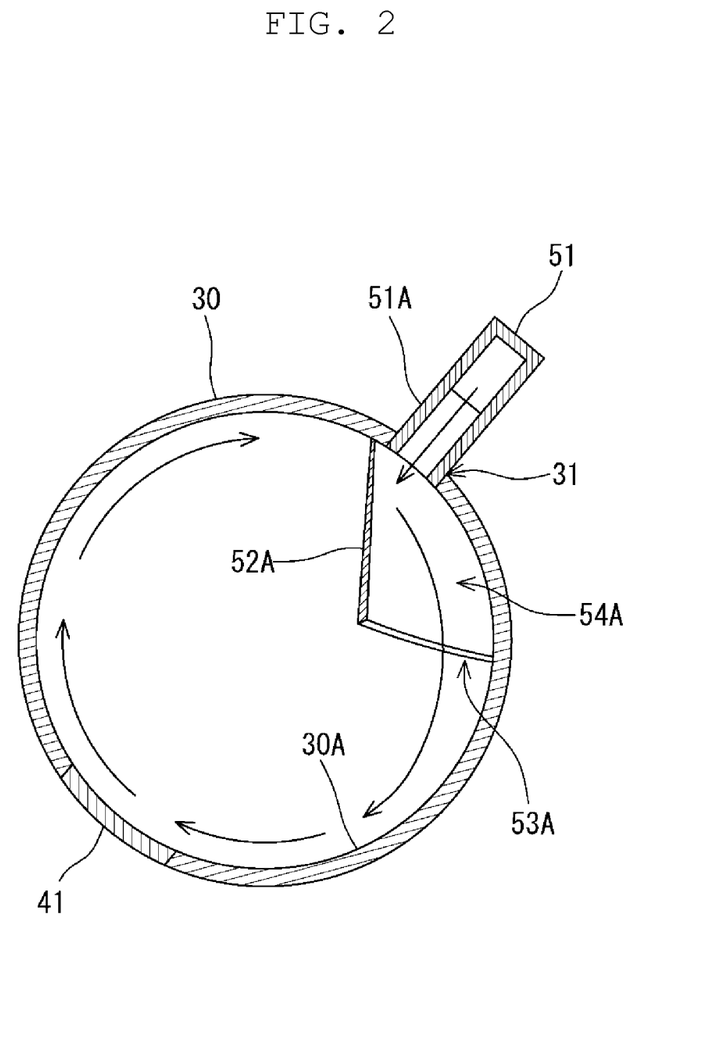
FIG. 2 is a schematic sectional view sectioned along line A-A of FIG. 1 of an alga tank and a supplying portion that the alga growing apparatus to which the present invention is applied includes.
Figure 3:
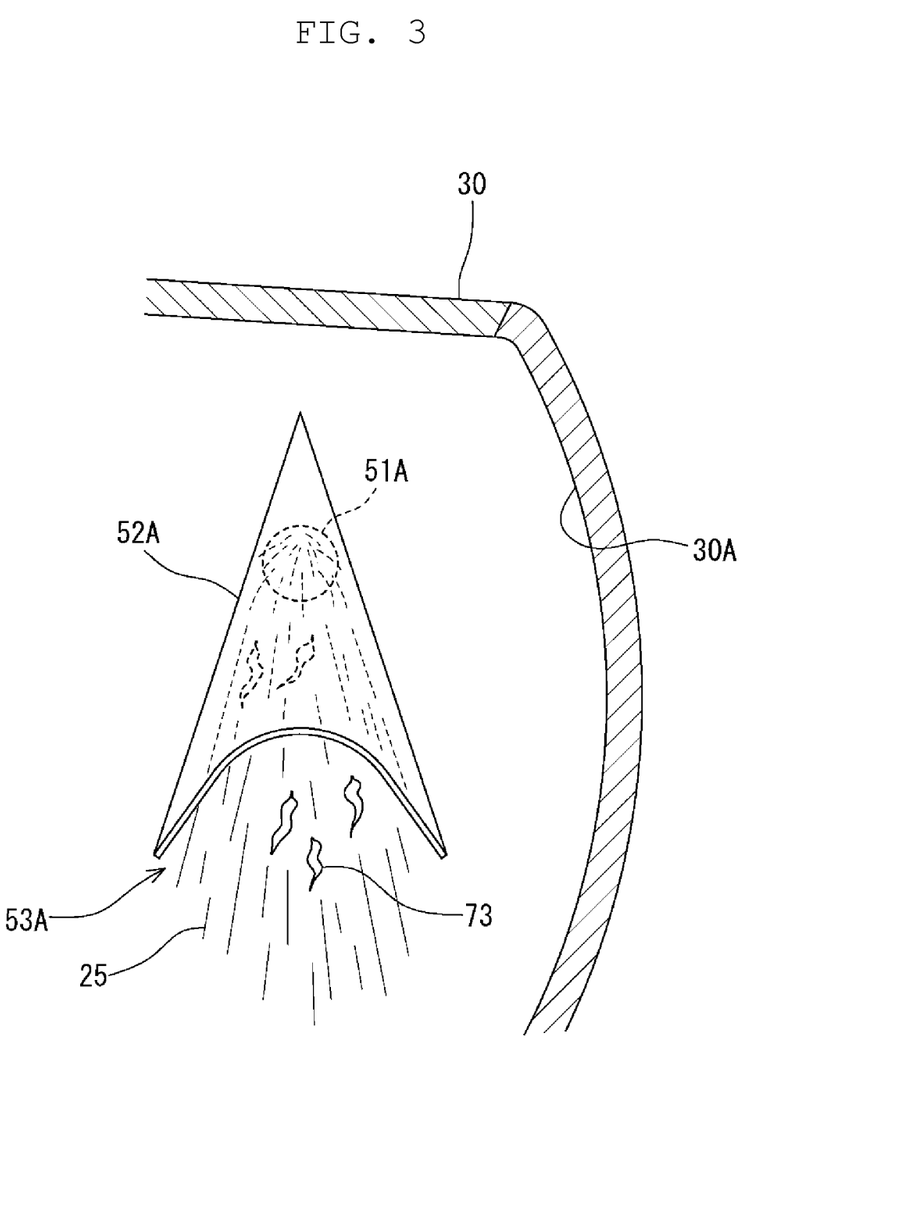
FIG. 3 is a schematic view showing an example of a condition in which growing water and nori thalli are discharged from a first discharge port of a first cover body of the supplying portion that the alga growing apparatus to which the present invention is applied includes.

FIG. 1 is a schematic view for describing an example of an alga growing apparatus to which the present invention is applied. Also, FIG. 2 is a schematic sectional view sectioned along line A-A of FIG. 1 of an alga tank and a supplying portion that the algae growing apparatus to which the present invention is applied includes. Also, FIG. 3 is a schematic view showing an example of a condition in which growing water and nori thalli are discharged from a first discharge port of a first cover body of the supplying portion that the alga growing apparatus to which the present invention is applied includes.

The alga growing apparatus 10 according to the present invention shown in FIG. 1 includes a gas dissolving portion 20.

Here, the gas dissolving portion 20 is capable of dissolving carbon dioxide and oxygen into a liquid, for example, deep-ocean water and forming the growing water 25 that is a solution.

That is, a carbon dioxide supply pipe 21 for supplying the carbon dioxide into an interior of the gas dissolving portion 20 is connected in communication with the gas dissolving portion 20.

Also, an oxygen supply pipe 22 for supplying the oxygen into the interior of the gas dissolving portion 20 is connected in communication with the gas dissolving portion 20.

Also, the carbon dioxide supply pipe 21 has an unillustrated supply pressure adjusting mechanism such as to enable the carbon dioxide to be supplied into the gas dissolving portion 20 at a supply pressure, for example, of 1.2 hPa.

Also, the oxygen supply pipe 22 has an unillustrated supply pressure adjusting mechanism such as to enable the oxygen to be supplied into the gas dissolving portion 20 at a supply pressure, for example, of 1.2 hPa.

Also, the deep-ocean water is supplied into the gas dissolving portion 20 at a supply pressure lower than the supply pressure of the carbon dioxide and the supply pressure of the oxygen.

That is, the deep-ocean water is made to flow into an atmosphere inside the gas dissolving portion 20 that is filled with the carbon dioxide and the oxygen while being maintained at a lower pressure than the pressure of the carbon dioxide and the pressure of the oxygen and thereby made to contact the carbon dioxide and the oxygen and the carbon dioxide and the oxygen is dissolved into the deep-ocean water.

In this process, by there being a pressure difference between the pressure of the deep-ocean water and the pressure of the carbon dioxide, the carbon dioxide of high pressure enters into the gaps between molecules of the deep-ocean water, nitrogen, etc., that had entered between the molecules of the deep-ocean water are oppositely driven out, and replacement of gas is performed.

The growing water 25 in which the carbon dioxide is dissolved and is high in dissolved carbon dioxide amount is thereby obtained.

Also, by there being a pressure difference between the pressure of the deep-ocean water and the pressure of the oxygen as well, the oxygen of high pressure enters into gaps between molecules of the deep-ocean water, the nitrogen, etc., that had entered into the gaps between the molecules of the deep-ocean water are oppositely driven out, and replacement of gas is performed.

The growing water 25 in which the oxygen is dissolved and is high in dissolved oxygen amount is thereby obtained.

Also, the gas dissolving portion does not necessarily have to dissolve oxygen.

Also, the alga growing apparatus 10 according to the present invention includes the alga tank 30.

Here, the alga tank 30 is capable of containing the growing water 25. Also, algae, for example, the nori thalli 73 are placed in the growing water 25 and therefore, the alga tank 30 is also capable of containing the nori thalli 73 placed in the growing water 25.

Also, instead of the nori thalli, unicellular microalgae such as *Spirulina*, etc., can be placed in the growing water to cultivate the unicellular microalgae.

Also, an inner side surface 30A of the alga tank 30 that contacts the contained growing water 25 and the nori thalli 73 is curved.

That is, the alga tank 30 has a circular cylindrical shape that extends in one direction and with which both ends in the direction of extension are closed and a cross-sectional shape in a direction substantially orthogonal to the direction of extension is substantially circular.

Also, a length, that is, a length in the direction of extension of the alga tank 30 is not restricted in particular and can be set, for example, to 25 m.

Also, an air pressure of an exterior of the alga tank 30 is atmospheric pressure (1.0 hPa) and since the growing water 25 is seawater into which the carbon dioxide and the oxygen are dissolved at higher supply pressures than atmospheric pressure, a pressure of the growing water 25 is higher than the pressure of the exterior of the alga tank 30.

That is, the gas dissolving portion 20 is capable of forming the growing water 25 having a higher pressure than the pressure of the exterior of the alga tank 30.

Also, the alga growing apparatus 10 according to the present invention includes a plurality of first LEDs 40 and a plurality of second LEDs 41.

Here, the plurality of first LEDs 40 are arrayed in series at predetermined intervals of, for example, 1 m from each other in the same direction as the direction of extension of the alga tank 30.

Also, the plurality of second LEDs 41 are arrayed in series at predetermined intervals of, for example, 1 m from each other in the same direction as the direction of extension of the alga tank 30 as well.

Also, as shown in FIG. 1, a serial array that the plurality of first LEDs 40 constitute and a serial array that the plurality of second LEDs 41 constitute oppose each other.

Also, the number of LEDs on a line that is substantially orthogonal to the direction of extension of the alga tank 30 and connects the array of first LEDs 40 and the array of second LEDs 41 is one. That is, a second LED 41 is not disposed at a position opposing a first LED 40 and, meanwhile, a first LED 40 is also not disposed at a position opposing a second LED 41.

Also, light emitting surfaces of the first LEDs 40 and light emitting surfaces of the second LEDs 41 are respectively positioned within the same surface as the inner side surface 30A of the alga tank 30 and are also positioned within the same surface as an outer side surface at an opposite side to the inner side surface 30A.

That is, the first LEDs 40 and the second LEDs 41 are embedded in a wall of the alga tank 30.

Also, although an illuminance and a wavelength of light emitted by the first LEDs 40 and the second LEDs 41 is not restricted in particular, if, for example, light having an illuminance of 3800 to 4200 lux and preferably 4000 lux and having a wavelength of 450 to 650 nm is emitted, this would be preferable because algae grow the most in this case.

Also, the first LEDs and the second LEDs are one example of light emitters.

Also, the alga growing apparatus 10 according to the present invention includes a carbon dioxide concentration sensor 42 capable of detecting a concentration of the carbon dioxide in the growing water 25 contained in the alga tank 30 and an oxygen concentration sensor 43 capable of detecting a concentration of the oxygen in the growing water 25 contained in the alga tank 30.

Here, the carbon dioxide concentration sensor 42 and the oxygen concentration sensor 43 are mounted on the wall of the alga tank 30 and portions thereof project to an interior of the alga tank 30.

Also, although the carbon dioxide concentration and the oxygen concentration are not restricted in particular, if the carbon dioxide concentration is 2.0 to 3.5%, this would be preferable because algae grow the most in this case.

In particular, if growing water with which the carbon dioxide concentration is 2.0% is used, a growth rate of algae becomes approximately 24 times that in the case of using natural seawater.

Also, the alga growing apparatus 10 according to the present invention includes a controller 44 capable of communication with the carbon dioxide concentration sensor 42 and the oxygen concentration sensor 43.

Also, the controller 44 is mounted to the gas dissolving portion 20.

Also, the controller 44 is capable of control such that if the carbon dioxide concentration detected by the carbon dioxide concentration sensor 42 is less than a predetermined value, for example, the gas dissolving portion 20 is made to set a state of communication with the carbon dioxide supply pipe 21 to an "open" state and make more carbon dioxide dissolve into the growing water 25.

Also, the controller 44 is capable of control such that if the oxygen concentration detected by the oxygen concentration sensor 43 is less than a predetermined value, for example, the gas dissolving portion 20 is made to set a state of communication with the oxygen supply pipe 22 to an "open" state and make more oxygen dissolve into the growing water 25.

Also, the alga growing apparatus 10 according to the present invention can also include a temperature sensor, a pressure sensor, etc., and further, the controller 44 may have an artificial intelligence function.

Also, the alga growing apparatus 10 according to the present invention includes the supplying portion 50.

Here, the supplying portion 50 is in communication with the gas dissolving portion 20.

That is, one end of a growing water supply pipe 23 is connected in communication with the gas dissolving portion 20 and another end of the growing water supply pipe 23 at an opposite side to the one end is connected in communication with the supplying portion 50.

Also, the supplying portion 50 is capable of discharging the growing water 25 along a curving direction of the inner side surface 30A of the alga tank 30 or a direction that obliquely intersects the curving direction.

Consequently, the growing water 25 flows inside the alga tank 30 as an eddy flow as shown in FIG. 2.

Also, the supplying portion 50 is in communication with the alga tank 30.

That is, the supplying portion 50 has a supply pipe 51.

Here, a plurality of penetrating holes putting the interior and the exterior of the alga tank 30 in communication are formed in the inner side surface 30A of the alga tank 30 and the supply pipe 51 is connected in communication with the plurality of penetrating holes respectively via a plurality of branch supply pipes.

That is, the supply pipe 51 is connected in communication with the plurality of penetrating holes of the alga tank 30 respectively via a first branch supply pipe 51A, a second branch supply pipe 51B, and a third branch supply pipe 51C.

For example, as shown in FIG. 2, one end of the first branch supply pipe 51A is connected in communication with a first supplying penetrating hole 31 formed in the alga tank 30 and another end of the first branch supply pipe 51A at an opposite side to the one end is connected in communication with the supply pipe 51.

Also, although unillustrated, one end of the second branch supply pipe 51B is connected in communication with a second supplying penetrating hole formed in the alga tank 30 and another end of the second branch supply pipe 51B is connected in communication with the supply pipe 51.

Also, although unillustrated, one end of the third branch supply pipe 51C is connected in communication with a third supplying penetrating hole formed in the alga tank 30 and another end of the third branch supply pipe 51C is connected in communication with the supply pipe 51.

Also, the supplying portion 50 has a first cover body 52A, a second cover body 52B, and a third cover body 52C.

Here, the first cover body 52A is disposed on a first supplying penetrating hole central axis extending in a direction substantially orthogonal to a line joining opposing edge portions of the first supplying penetrating hole 31.

Here, the first supplying penetrating hole central axis is an intangible, imaginary line.

Also, the first cover body 52A is mounted to the inner side surface 30A of the alga tank 30.

Also, the first cover body 52A forms, with the inner side surface 30A of the alga tank 30, a first discharge space 54A in communication with the first branch supply pipe 51A.

Also, the first cover body 52A has formed therein the first discharge port 53A that is an opening portion putting the first discharge space 54A and the interior of the alga tank 30 in communication and facing a direction intersecting the direction of extension of the alga tank 30.

Also, a surface of the first cover body 52A at an opposite side to a surface facing the first discharge space 54A is curved.

Also, although unillustrated, the second cover body 52B and the third cover body 52C, like the first cover body 52A, also form discharge spaces with the inner side surface 30A of the alga tank 30 and further have formed therein discharge ports putting the discharge spaces and the interior of the alga tank 30 in communication and facing a direction intersecting the direction of extension of the alga tank 30.

The growing water 25 discharged from the first branch supply pipe 51A, the second branch supply pipe 51B, and the third branch supply pipe 51C respectively hits the first cover body 52A, the second cover body 52B, and the third cover body 52C respectively and a direction in which the growing water 25 flows is directed toward the inner side surface 30A of the alga tank 30.

The supplying portion 50 can thus make the growing water 25 flow along the curved inner side surface 30A of the alga tank 30.

Also, although with the example shown in FIG. 1, the number of branch supply pipes and the number of corresponding cover bodies are 3, the numbers are obviously not restricted thereto.

By increasing the number of branch supply pipes and the number of corresponding cover bodies, an even stronger eddy flow can be generated.

Also, the alga growing apparatus 10 according to the present invention includes a circulation pump portion 60.

Here, the circulation pump portion 60 is in communication with the alga tank 30 and the gas dissolving portion 20.

That is, one end of a sucking-out pipe 61 is connected in communication with the alga tank 30 and another end of the sucking-out pipe 61 at an opposite side to the one end is connected in communication with the circulation pump portion 60.

Here, a sucking-out penetrating hole 32 that is a penetrating hole putting the interior and the exterior of the alga tank 30 in communication is formed at one end portion of the alga tank 30 and the one end of the sucking-out pipe 61 is connected in communication with the sucking-out penetrating hole 32.

Also, one end of a delivery pipe 62 is connected in communication with the circulation pump portion 60 and another end of the delivery pipe 62 at an opposite side to the one end is connected in communication with the gas dissolving portion 20.

Also, the circulation pump portion 60 is capable of sucking out the growing water 25 and the nori thalli 73 contained in the alga tank 30 from the alga tank 30.

Also, the circulation pump portion 60 is capable of delivering the sucked-out growing water 25 and nori thalli 73 to the gas dissolving portion 20 and, by a force in the process of delivery, making the growing water 25 and the nori thalli 73 pass through the gas dissolving portion 20 and the supply pipe 51 and injecting the growing water 25 and the nori thalli 73 into the alga tank 30 from the first branch supply pipe 51A, the second branch supply pipe 51B, and the third branch supply pipe 51C.

Also, the gas dissolving portion 20 is capable of dissolving carbon dioxide and oxygen into the growing water 25 delivered to the gas dissolving portion 20 together with the nori thalli 73.

Also, the alga growing apparatus 10 according to the present invention includes a nori thalli supplying portion 70.

Here, the nori thalli supplying portion 70 is in communication with the supplying portion 50 and is capable of supplying the nori thalli 73 to the supplying portion 50.

That is, one end of a nori thalli supply pipe 71 is connected in communication with the nori thalli supplying portion 70 and another end of the nori thalli supply pipe 71 at an opposite side to the one end is connected in communication with the growing water supply pipe 23.

Here, the growing water supply pipe 23 is connected in communication with the supplying portion 50 and therefore, the nori thalli supplying portion 70 is in communication with the supplying portion 50 via the nori thalli supply pipe 71 and the growing water supply pipe 23.

Also, the alga tank 30 is disposed in a state where the direction of extension of the alga tank 30 intersects a horizontal direction.

Also, a position of the one end portion of the alga tank 30 at which the sucking-out penetrating hole 32 that is a sucking-out part at which the growing water 25 and the nori thalli 73 are sucked out from the alga tank 30 is located lower in a vertical direction than a position of another end portion at the opposite side to the one end portion.

That is, the alga tank 30 has the respective end portions supported by a set of alga tank supporting portions 35 that differ in height and is disposed inclinedly.

Also, the direction that the first discharge port 53 of the first cover body 52A faces is a direction obliquely intersecting the direction of extension of the alga tank 30 and is a direction directed toward the one end portion of the alga tank 30 at which the sucking-out penetrating hole 32 is formed.

Also, the direction that the second discharge port of the second cover body 52B faces and the direction that the third discharge port of the third cover body 52C faces are the same direction as the direction that the first discharge port 53 of the first cover body 52A faces.

Also, an unloading penetrating hole 33 that is a penetrating hole putting the interior and the exterior of the alga tank 30 in communication is formed at a surface that is the same end portion as the end portion of the alga tank 30 at which the sucking-out penetrating hole 32 is formed and is substantially orthogonal to the direction of extension of the alga tank 30.

Also, one end of an unloading pipe 36 is connected in communication with the unloading penetrating hole 33.

Also, another end of the unloading pipe 36 at an opposite side to the one end is connected in communication with a nori storage tank 80 for storing the nori thalli 73 that have grown to a length of approximately 15 cm together with the growing water 25.

Also, the unloading pipe 36 is connected in communication with the same end portion as the end portion of the alga tank 30 at which the sucking-out penetrating hole 32 is formed and therefore a slope of the alga tank 30 can be used to unload the growing water 25 and the nori thalli 73.

Also, an air vent penetrating hole 34 that is a penetrating hole putting the interior and the exterior of the alga tank 30 in communication is formed in the other end portion at the opposite side to the one end portion of the alga tank 30 at which the sucking-out penetrating hole 32 and the unloading penetrating hole 33 are formed.

The air vent penetrating hole 34 is a penetrating hole for venting air inside the alga tank 30 when unloading the growing water 25 and the nori thalli 73 from the alga tank 30 by the unloading pipe 36.

Also, the alga growing apparatus 10 according to the present invention includes a liquid fertilizer injecting portion 90.

Here, the liquid fertilizer injecting portion 90 is in communication with the supplying portion 50 and is capable of injecting a liquid fertilizer into the supplying portion 50.

That is, one end of a liquid fertilizer supply pipe 91 is connected in communication with the liquid fertilizer injecting portion 90 and another end of the liquid fertilizer supply pipe 91 at an opposite side to the one end is connected in communication with the growing water supply pipe 23.

Here, the growing water supply pipe 23 is connected in communication with the supplying portion 50 and therefore, the liquid fertilizer injecting portion 90 is in communication with the supplying portion 50 via the liquid fertilizer supply pipe 91 and the growing water supply pipe 23.

Also, the alga growing apparatus 10 according to the present invention includes a seawater injecting portion 100.

Here, the seawater injecting portion 100 is in communication with the gas dissolving portion 20.

That is, one end of a seawater supply pipe 103 is connected in communication with the seawater injecting portion 100 and another end of the seawater supply pipe 103 at an opposite side to the one end is connected in communication with the delivery pipe 62 that is connected in communication with the gas dissolving portion 20.

Although the seawater injecting portion 100 is thus in communication with the gas dissolving portion 20 via the delivery pipe 62, it can obviously be put in communication with the gas dissolving portion 20 directly and not via the delivery pipe 62.

Also, one end of a seawater suction pipe 101 is connected in communication with the seawater injecting portion 100 and another end of the seawater suction pipe 101 at an opposite side to the one end is in communication with a seawater storage tank 105 that stores the deep-ocean water.

The seawater injecting portion 100 is thus capable of injecting the deep-ocean water into the gas dissolving portion 20.

Also, the alga growing apparatus 10 according to the present invention includes a sterilization treatment portion 106.

Here, the sterilization treatment portion 106 is connected in communication with the seawater suction pipe 101 and is capable of sterilization treatment of the deep-ocean water flowing through the seawater suction pipe 101.

Also, the sterilization treatment portion 106 performs sterilization treatment of the deep-ocean water by specifically using, for example, ozone or ultraviolet rays.

Also, the seawater injecting portion is an example of a liquid injecting portion.

Also, the deep-ocean water does not have to be used as the liquid and, for example, groundwater can also be used.

Also, the alga growing apparatus 10 according to the present invention includes a growing water supply control valve 24 mounted to the growing water supply pipe 23.

Also, the alga growing apparatus 10 according to the present invention includes an unloading control valve 37 mounted to the unloading pipe 36.

Also, the alga growing apparatus 10 according to the present invention includes an air vent control valve 38 mounted to the air vent penetrating hole 34.

Also, the alga growing apparatus 10 according to the present invention includes a delivery control valve 63 mounted to the delivery pipe 62.

Also, the alga growing apparatus 10 according to the present invention includes a nori thalli supply control valve 72 mounted to the nori thalli supply pipe 71.

Also, the alga growing apparatus 10 according to the present invention includes a liquid fertilizer supply control valve 92 mounted to the liquid fertilizer supply pipe 91.

Also, the alga growing apparatus 10 according to the present invention includes a seawater suction control valve 102 mounted to the seawater suction pipe 101.

Also, the alga growing apparatus 10 according to the present invention includes a seawater supply control valve 104 mounted to the seawater supply pipe 103.

These control valves can be controlled based on control signals transmitted by a smartphone 107.

That is, the growing water supply control valve 24 can be controlled based on a control signal transmitted by the smartphone 107 to control a flow rate of the growing water 25 and the nori thalli 73 placed in the growing water 25 flowing from the gas dissolving portion 20 to the alga tank 30.

Also, the unloading control valve 37 can be controlled based on a control signal transmitted by the smartphone 107 to control a flow rate of the growing water 25 and the nori thalli 73 placed in the growing water 25 unloaded from the alga tank 30.

Also, the air vent control valve 38 can be controlled based on a control signal transmitted by the smartphone 107 to control opening/closing of the air vent penetrating hole 34.

Also, the delivery control valve 63 can be controlled based on a control signal transmitted by the smartphone 107 to control a flow rate of the growing water 25 and the nori thalli 73 placed in the growing water 25 sucked out from the alga tank 30 and delivered to the gas dissolving portion 20.

Also, the nori thalli supply control valve 72 can be controlled based on a control signal transmitted by the smartphone 107 to control a supply amount of the nori thalli 73 to the supplying portion 50.

Also, the liquid fertilizer supply control valve 92 can be controlled based on a control signal transmitted by the smartphone 107 to control a supply amount of the liquid fertilizer to the supplying portion 50.

Also, the seawater suction control valve 102 and the seawater supply control valve 104 can be controlled based on control signals transmitted by the smartphone 107 to control a supply amount of the deep-ocean water to the gas dissolving portion 20.

Also, these control valves can be arranged to be controlled based on control signals transmitted by a tablet terminal or other portable terminal besides a smartphone.

Also, although unillustrated, the alga growing apparatus 10 according to the present invention is disposed in a temperature-controlled room and a plurality of the alga tanks 30 are disposed in parallel.

With the alga growing apparatus according to the present invention, the supplying portion does not necessarily have to have the cover bodies.

However, it is preferable for the cover bodies to be provided because algae would be less likely to become caught in the supplying portion than an arrangement not having the cover bodies and with which the supply pipe is projected from the inner side surface of the alga tank.

Also, with the alga growing apparatus according to the present invention, the plurality of LEDs, that is, light emitters do not necessarily have to be arrayed in series at predetermined intervals from each other in the same direction as the direction of extension of the alga tank and, for example, can be arrayed in a direction substantially orthogonal to the direction of extension of the alga tank.

However, an arrangement where the plurality of light emitters are arrayed in series at predetermined intervals from each other in the same direction as the direction of extension of the alga tank, there are a plurality of serial arrays of the light emitters, and the number of light emitters on a line substantially orthogonal to the direction of extension of the alga tank and connecting two arrays that oppose each other is one is preferable because a light emitting capability can be maintained while suppressing a size per unit of the light emitters and the number of the light emitters.

Also, with the alga growing apparatus according to the present invention, the alga tank does not necessarily have to be disposed inclinedly and also, the direction that the discharge port, that is, the opening portion of each cover body faces does not necessarily have to be a direction obliquely intersecting the direction of extension of the alga tank and directed toward the one end portion of the alga tank at which the sucking-out part is formed.

However, it is preferable for the alga tank to be disposed inclinedly and the direction that the opening portion of each cover body faces to be a direction obliquely intersecting the direction of extension of the alga tank and directed toward the one end portion of the alga tank at which the sucking-out part is formed because the nori thalli, that is, the algae would then gather easily toward the sucking-out part due to gravity and a force of flow of the growing water, that is, the solution, and the solution and the algae can be circulated even if a length of extension of the alga tank is made comparatively long.

Also, the alga growing apparatus according to the present invention does not necessarily have to include the liquid fertilizer injecting portion.

Also, the alga growing apparatus according to the present invention does not necessarily have to include the control valves that are controllable based on signals transmitted by the smartphone, that is, the portable terminal.

However, it is preferable for the liquid fertilizer injecting portion to be provided because the growth of algae can then be promoted and it is also preferable for the control valves to be provided because it would then be possible to control a flow rate of the solution passing through a communicating pipe or an unloading amount of the solution from the alga tank by a single operation of the portable terminal.

Next, an alga growing method according to the present invention that uses the alga growing apparatus according to the present invention shall be described.

That is, the alga growing method according to the present invention includes a growing water forming step that is a solution forming step of forming the growing water 25 that is the solution by dissolving carbon dioxide having a higher pressure than a pressure of a liquid, for example, the deep-ocean water into the deep-ocean water in the gas dissolving portion 20 capable of dissolving the carbon dioxide into the deep-ocean water.

Also, the alga growing method according to the present invention includes a discharging step of supplying the growing water 25 to the alga tank 30 having the curved inner side surface 30A and making the growing water 25 flow along the inner side surface 30A of the alga tank 30.

Also, the alga growing method according to the present invention includes a nori thalli supplying step of supplying the nori thalli 73 to the alga tank 30.

Also, the alga growing method according to the present invention includes a light emitting step of emitting light toward the interior of the alga tank 30 containing the growing water 25 and the nori thalli 73 placed in the growing water 25.

Also, the alga growing method according to the present invention includes a circulating step of sucking out the growing water 25 and the nori thalli 73 from the alga tank 30 and introducing the growing water 25 and the nori thalli 73 into the gas dissolving portion 20.

Also, the alga growing method according to the present invention includes an unloading step of unloading the nori thalli 73 from the alga tank 30.

Also, the alga growing method according to the present invention includes a cutting step of cutting the unloaded nori thalli.

Also, in the nori thalli supplying step, the nori thalli 73 having a length shorter than a length of the nori thalli 73 unloaded in the unloading step is supplied.

Although the alga growing method according to the present invention does not necessarily have to include the cutting step, it is preferable for the cutting step to be provided because a portion of the grown nori thalli can then be reused and the nori thalli can be cultivated semi-permanently.

Procedures of algae growing using the alga growing apparatus according to the present invention shall now be described even more specifically.

Here, in FIG. 1, thin arrows represent flow of liquid and solid and thick arrows represent flow of gas.

The nori thalli supplying portion 70 supplies the nori thalli 73 having a length of approximately 1 cm to the alga tank 30 via the supplying portion 50 to perform the nori thalli supplying step.

In this process, an amount of the nori thalli 73 supplied to the alga tank 30 is adjusted by the nori thalli supply control valve 72.

Also, the seawater injecting portion 100 suctions the deep-ocean water stored in the seawater storage tank 105 and injects the deep-ocean water into the gas dissolving portion 20.

In this process, the sterilization treatment portion 106 performs the sterilization treatment on the deep-ocean water flowing through the seawater suction pipe 101.

Then in the gas dissolving portion 20, the growing water forming step is performed by dissolving the carbon dioxide having the pressure higher than the pressure of the deep-ocean water into the injected deep-ocean water to form the growing water 25 that is the solution.

In this process, the oxygen having the pressure higher than the pressure of the deep-ocean water is also dissolved into the injected deep-ocean water in the gas dissolving portion 20.

Also, the growing water 25 formed in the gas dissolving portion 20 is fed to the supplying portion 50 through the growing water supply pipe 23 and the growing water 25 is supplied to the alga tank 30 through the first branch supply pipe 51A, the second branch supply pipe 51B, and the third branch supply pipe 51C of the supplying portion 50.

And since the nori thalli 73 have already been supplied to the alga tank 30, when the interior of the alga tank 30 becomes filled with the growing water 25, the nori thalli 73 becomes suspended inside the growing water 25 and the circulation pump portion 60 sucks out the growing water 25 and the nori thalli 73 together.

Also, the circulation pump portion 60 introduces the sucked-out growing water 25 and nori thalli 73 to the gas dissolving portion 20.

In this process, the sucked-out growing water 25 and nori thalli 73 pass through the sucking-out pipe 61, further pass through the delivery pipe 62, and are fed to the gas dissolving portion 20.

Also, the circulation pump portion 60 introduces the growing water 25 and the nori thalli 73 into the gas dissolving portion 20, further introduces the growing water 25 and the nori thalli 73 into the supplying portion 50 upon passage through the gas dissolving portion 20, and with that momentum, injects the growing water 25 and the nori thalli 73 into the alga tank 30 from the first branch supply pipe 51A, the second branch supply pipe 51B, and the third branch supply pipe 51C of the supplying portion 50.

In this process, the supplying portion 50 discharges the growing water 25 and the nori thalli 73 along directions obliquely intersecting the curving direction of the inner side surface 30A of the alga tank 30.

The circulating step and the discharging step are thus performed.

Also, the gas dissolving portion 20 dissolves the carbon dioxide and the oxygen into the growing water 25 introduced together with the nori thalli 73 into the gas dissolving portion 20.

Also, the plurality of first LEDs 40 and the plurality of second LEDs 41 are made to emit light and light is emitted toward the interior of the alga tank 30 containing the growing water 25 and the nori thalli 73 placed in the growing water 25 to perform the light emitting step.

Then when the length of the nori thalli 73 has become approximately 15 cm, the unloading control valve 37 is opened and the nori thalli 73 are unloaded together with the growing water 25 from the alga tank 30 through the unloading pipe 36 to perform the unloading step.

Here, the length of the nori thalli 73 can be measured, for example, by taking an image of the nori thalli 73 from the exterior of the alga tank 30 and analyzing the image obtained by the image taking.

Also, the unloaded nori thalli 73 are cut to a length of approximately 1 cm to perform the cutting step.

Also, when the alga growing method according to the present invention was performed using the alga growing apparatus 10 according to the present invention, it was possible to grow the nori thalli to approximately 15 cm approximately 24 hours after supplying the nori thalli of approximately 1 cm length to the alga tank.

As described above, the alga growing apparatus according to the present invention includes the gas dissolving portion, the LEDs, that is, the light emitters, and the circulation pump portion and therefore, photosynthesis can be promoted inside the alga tank.

Also, the alga growing apparatus according to the present invention includes the alga tank and the supplying portion and can therefore generate the eddy flow of the growing water, that is, the solution inside the alga tank and can illuminate the light from the light emitters uniformly on the nori thalli, that is, the algae.

Also, by the eddy flow, oxygen bubbles formed by photosynthesis are easily separated from the algae and the algae are thereby enabled to absorb carbon dioxide easily.

Also, the alga growing apparatus according to the present invention includes the circulation pump portion and since the algae are thus passed through the gas dissolving portion together with the solution, the carbon dioxide can be supplied sufficiently to the algae in the gas dissolving portion.

The alga growing apparatus according to the present invention can thus improve growing efficiency of algae.

Also, the alga growing method according to the present invention can also improve the growing efficiency of algae because the algae are grown using the alga growing apparatus according to the present invention.

In particular, since the nori thalli are used, growing can be completed faster than a method of cultivating by supplying spores or protonemata of nori.

DESCRIPTION OF REFERENCE NUMERALS

10 Alga growing apparatus
20 Gas dissolving portion
21 Carbon dioxide supply pipe
22 Oxygen supply pipe
23 Growing water supply pipe
24 Growing water supply control valve
25 Growing water
30 Alga tank
30A Inner side surface
31 First supplying penetrating hole
32 Sucking-out penetrating hole
33 Unloading penetrating hole
34 Air vent penetrating hole
35 Alga tank supporting portion
36 Unloading pipe
37 Unloading control valve
38 Air vent control valve
40 First LED
41 Second LED
42 Carbon dioxide concentration sensor
43 Oxygen concentration sensor
44 Controller
50 Supplying portion
51 Supply pipe
51A First branch supply pipe
51B Second branch supply pipe
51C Third branch supply pipe
52A First cover body
52B Second cover body
52C Third cover body
53A First discharge port
54A First discharge space
60 Circulation pump portion
61 Sucking-out pipe 62 Delivery pipe
63 Delivery control valve
70 Nori thalli supplying portion
71 Nori thalli supply pipe
72 Nori thalli supply control valve
73 Nori thalli
80 Nori storage tank
90 Liquid fertilizer injecting portion
91 Liquid fertilizer supply pipe
92 Liquid fertilizer supply control valve
100 Seawater injecting portion
101 Seawater suction pipe
102 Seawater suction control valve
103 Seawater supply pipe
104 Seawater supply control valve
105 seawater storage tank
106 Sterilization treatment portion
107 Smartphone

What is claimed is:

1. An alga growing apparatus comprising:
a gas dissolving portion configured to dissolve carbon dioxide into a liquid to form a solution;
an alga tank which includes a curved inner side surface wherein the alga tank is constructed to hold the solution and algae that is placed in the solution, and wherein the inner side surface is in contact with the solution and the algae;
a light emitter configured to emit light towards an interior of the alga tank;
a supplying portion that is communicative with the gas dissolving portion and the alga tank wherein the supplying portion is configured to discharge the solution along a direction obliquely intersecting a curved direction; and
a circulation pump portion that is communicative with the alga tank and the gas dissolving portion, wherein the circulation pump portion is configured to suck out the solution and the algae from the alga tank, and, if the solution and the algae were sucked out from the alga tank, to inject the solution and algae from the supplying portion into the alga tank through the gas dissolving portion,
wherein the alga tank is shaped substantially cylindrical that extends in one direction forming an extension with both ends of the alga tank being closed, wherein the alga tank is inclined,
wherein a cross-sectional shape of the alga tank is substantially circular,
wherein the supplying portion includes a supply pipe that is connected and communicative with a penetrating hole formed in the inner side surface of the alga tank,
wherein the penetrating hole puts the interior and an exterior of the alga tank in communication,
wherein the supplying portion further includes a cover body that is formed within the alga tank and disposed around the penetrating hole and over the penetrating hole and downwardly extends in a direction substantially orthogonal to a central axis line of the penetrating hole obliquely along the inner side surface of the alga tank such that the solution and algae coming out of the supply pipe is discharged through the penetrating hole in a direction of the central axis line of the penetrating hole and obliquely hit the cover body, thereby changing a flow direction of the solution and algae downwardly in order to make the solution and algae flow along the direction obliquely intersecting the curved direction of the inner side surface of the alga tank,
wherein the cover body widens downwardly with its top side being closed such that the flow direction of the solution and algae spreads out downwardly,
wherein the cover body is mounted to the inner side surface of the alga tank and forms, with the inner side surface of the alga tank, a space that is communicative with the supply pipe,
wherein the cover body includes an opening portion that is formed therein, and
wherein the opening portion of the cover body places the space of the cover body in communication with the interior of the alga tank,
wherein the opening portion of the cover body faces a direction that intersects a direction of the extension of the alga tank, and
wherein a surface of the cover body, which is an opposite side of a surface that faces the space of the cover body, is curved,
wherein the growing water is deep-ocean water,
wherein the alga growing apparatus further comprises a control valve and a sterilization treatment portion,
wherein the control valve is mounted to a communicating pipe,
wherein the sterilization treatment portion performs sterilization treatment of the deep-ocean water using ozone or ultraviolet rays, and
wherein a portable terminal is configured to transmit a signal that is recognized by the control valve such that the signal controls the control valve.

2. The alga growing apparatus according to claim 1, wherein the light emitter is a plurality of the light emitters arranged as a plurality of serial arrays of the light emitters,
wherein the light emitters in each of the serial arrays are arrayed in series at predetermined intervals and arranged in the direction of the extension of the alga tank, and
wherein the light emitters of one serial array and the light emitters of another serial array are not on a same line that is substantially orthogonal to the direction of extension of the alga tank.

3. The alga growing apparatus according to claim 1, further comprising a sucking-out part that is formed at one of the ends of the alga tank to suck out the solution and the algae,
wherein the end of the alga tank where the sucking-out part is formed is located lower in a vertical direction than a position of another end of the alga tank that lies on an opposite side to the one end,
wherein the opening portion of the cover body faces a direction obliquely intersecting the direction of extension of the alga tank and is directed towards the end portion of the alga tank where the sucking-out part is formed.

4. The alga growing apparatus according to claim 1, wherein the gas dissolving portion is configured to form a solution having a higher pressure than a pressure of the exterior of the alga tank.

5. The alga growing apparatus according to claim 1, comprising:
a liquid fertilizer injecting portion that is in communication with the supplying portion and is configured to inject a liquid fertilizer into the supplying portion;
a liquid injecting portion that is in communication with the gas dissolving portion and is configured to inject a liquid into the gas dissolving portion; and
wherein the communicating pipe connects the gas dissolving portion, the alga tank, the supplying portion, the circulation pump portion, the liquid fertilizer injecting portion, and the liquid injecting portion in mutual communication, wherein the communicating pipe is connected to an opening portion to make the interior of the alga tank communicative with the exterior of the alga tank, or to an unloading pipe that is connected communicatively with the opening portion, and.

6. An alga growing apparatus comprising:

a gas dissolving portion configured to dissolve carbon dioxide into a liquid to form a solution;

an alga tank which includes a curved inner side surface wherein the alga tank is constructed to hold the solution and algae that is placed in the solution, and wherein the inner side surface is in contact with the solution and the algae;

a light emitter configured to emit light towards an interior of the alga tank;

a supplying portion that is communicative with the gas dissolving portion and the alga tank wherein the supplying portion is configured to discharge the solution along a direction obliquely intersecting a curved direction; and a circulation pump portion that is communicative with the alga tank and the gas dissolving portion, wherein the circulation pump portion is configured to suck out the solution and the algae from the alga tank, and, if the solution and the algae were sucked out from the alga tank, to inject the solution and algae from the supplying portion into the alga tank through the gas dissolving portion, wherein the alga tank is shaped substantially cylindrical that extends in one direction forming an extension with both ends of the alga tank being closed, wherein the alga tank is inclined, wherein a cross-sectional shape of the alga tank is substantially circular, wherein the supplying portion includes a supply pipe that is connected and communicative with a penetrating hole formed in the inner side surface of the alga tank, wherein the penetrating hole puts the interior and an exterior of the alga tank in communication, wherein the supplying portion further includes a cover body that is formed within the alga tank and disposed around the penetrating hole and over the penetrating hole and downwardly extends in a direction substantially orthogonal to a central axis line of the penetrating hole obliquely along the inner side surface of the alga tank such that the solution and algae coming out of the supply pipe is discharged through the penetrating hole in a direction of the central axis line of the penetrating hole and obliquely hit the cover body, thereby changing a flow direction of the solution and algae downwardly in order to make the solution and algae flow along the direction obliquely intersecting the curved direction of the inner side surface of the alga tank, wherein the cover body widens downwardly with its top side being closed such that the flow direction of the solution and algae spreads out downwardly, wherein the cover body is mounted to the inner side surface of the alga tank and forms, with the inner side surface of the alga tank, a space that is communicative with the supply pipe, wherein the cover body includes an opening portion that is formed therein, and wherein the opening portion of the cover body places the space of the cover body in communication with the interior of the alga tank, wherein the opening portion of the cover body faces a direction that intersects a direction of the extension of the alga tank, and wherein a surface of the cover body, which is an opposite side of a surface that faces the space of the cover body, is curved.

\* \* \* \* \*